(12) United States Patent
Chen et al.

(10) Patent No.: US 8,557,104 B2
(45) Date of Patent: *Oct. 15, 2013

(54) IN VITRO ANALYTE SENSOR, AND METHODS

(71) Applicant: Abbott Diabetes Care Inc., Alameda, CA (US)

(72) Inventors: Ting Chen, Cedar Park, TX (US); Alexander G. Ghesquiere, San Francisco, CA (US)

(73) Assignee: Abbott Diabates Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/628,368

(22) Filed: Sep. 27, 2012

(65) Prior Publication Data

US 2013/0081959 A1    Apr. 4, 2013

Related U.S. Application Data

(63) Continuation of application No. 11/225,659, filed on Sep. 12, 2005, now Pat. No. 8,298,389.

(51) Int. Cl.
*G01N 33/487* (2006.01)
*G01N 27/26* (2006.01)
*C12Q 1/00* (2006.01)

(52) U.S. Cl.
USPC ...... 205/792; 600/365; 600/347; 204/403.01; 435/287.1; 422/68.1; 422/82.01

(58) Field of Classification Search
USPC ............. 204/403.01–403.15; 205/777.5, 778, 205/792; 600/345–348; 435/287.1; 422/68.1, 82.01
See application file for complete search history.

(56) References Cited

U.S. PATENT DOCUMENTS

| | | | |
|---|---|---|---|
| 5,120,420 A * | 6/1992 | Nankai et al. | 204/403.11 |
| 5,282,950 A | 2/1994 | Dietze et al. | |
| 5,288,636 A | 2/1994 | Pollmann et al. | |
| 5,352,351 A | 10/1994 | White et al. | |
| 5,437,999 A | 8/1995 | Diebold et al. | |
| 5,589,326 A | 12/1996 | Deng et al. | |
| 5,762,770 A | 6/1998 | Pritchard et al. | |
| 6,071,391 A | 6/2000 | Gotoh et al. | |

(Continued)

FOREIGN PATENT DOCUMENTS

| | | |
|---|---|---|
| EP | 0170375 | 2/1986 |
| EP | 0359831 | 3/1990 |

(Continued)

OTHER PUBLICATIONS

Bowyer et al., "Electrochemical Measurements in Submicrcliter Volumes," Anal. Chem., 64:459-462 (1992).

(Continued)

*Primary Examiner* — Jennifer Dieterle
(74) *Attorney, Agent, or Firm* — Edward J. Baba; Shweta Chandra; Bozicevic, Field & Francis LLP

(57) ABSTRACT

In vitro electrochemical sensor that provide accurate and repeatable analysis of a sample of biological fluid are provided. In some embodiments, the sensors have a measurement zone that has a volume less than the volume of the sample chamber. The measurement zone could have a volume of no more than about 0.2 μL.

20 Claims, 4 Drawing Sheets

(56) References Cited

U.S. PATENT DOCUMENTS

| | | | |
|---|---|---|---|
| 6,120,676 A * | 9/2000 | Heller et al. | 205/777.5 |
| 6,143,164 A | 11/2000 | Heller et al. | |
| 6,299,757 B1 | 10/2001 | Feldman et al. | |
| 6,338,790 B1 | 1/2002 | Feldman et al. | |
| 6,461,496 B1 | 10/2002 | Feldman et al. | |
| 6,551,494 B1 | 4/2003 | Heller et al. | |
| 6,576,101 B1 | 6/2003 | Heller et al. | |
| 6,591,125 B1 | 7/2003 | Buse et al. | |
| 6,592,745 B1 | 7/2003 | Feldman et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,749,740 B2 | 6/2004 | Liamos et al. | |
| 6,892,085 B2 | 5/2005 | McIvor et al. | |
| 8,298,389 B2 * | 10/2012 | Chen et al. | 204/403.11 |
| 2002/0157948 A2 * | 10/2002 | Liamos et al. | 204/403.01 |
| 2003/0212344 A1 | 11/2003 | Yuzhakov et al. | |
| 2004/0060818 A1 * | 4/2004 | Feldman et al. | 204/403.01 |
| 2004/0094433 A1 | 5/2004 | Neel et al. | |
| 2004/0225230 A1 | 11/2004 | Liamos et al. | |
| 2005/0019953 A1 | 1/2005 | Groll | |
| 2006/0147343 A1 | 7/2006 | Teramoto | |
| 2007/0108048 A1 | 5/2007 | Wang et al. | |

FOREIGN PATENT DOCUMENTS

| | | |
|---|---|---|
| EP | 1113264 | 7/2001 |
| JP | 5312761 | 11/1993 |
| JP | 2001208715 | 8/2001 |
| WO | WO 95/28634 | 10/1995 |
| WO | WO 97/00441 | 1/1997 |
| WO | WO 97/18465 | 5/1997 |
| WO | WO 98/02652 | 1/1998 |

OTHER PUBLICATIONS

Morris et al., "An Electrochemical Capillary Fill Device for the Analysis of Glucose Incorporating Glucose Oxidase and Ruthenium (III) Hexamine as Mediator," Electroanalysis, 4:1-9 (1992).

* cited by examiner

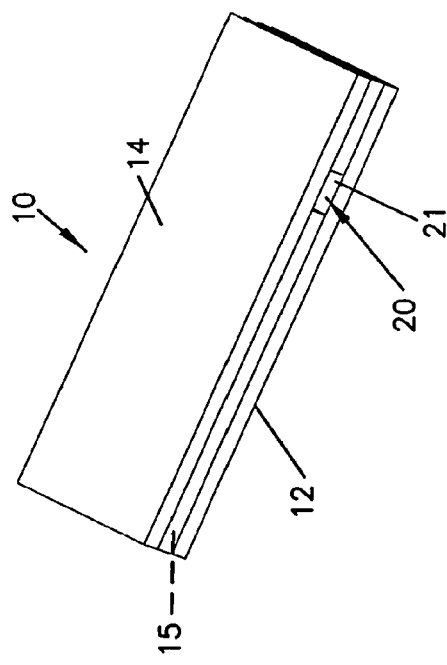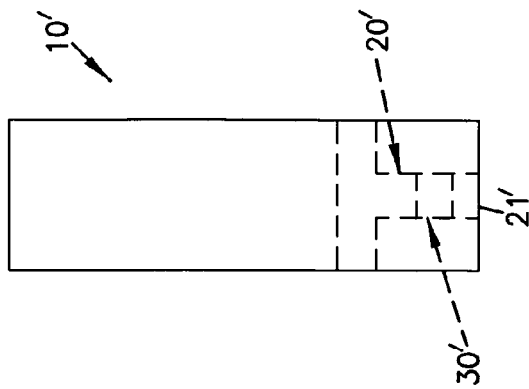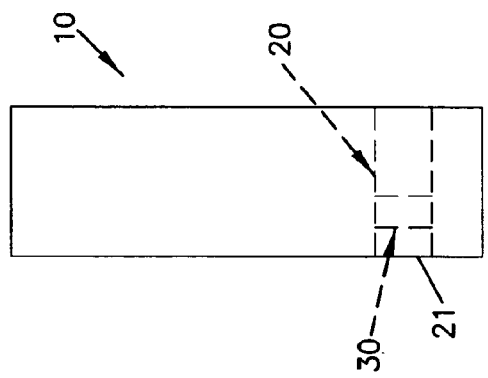

IN VITRO ANALYTE SENSOR, AND METHODS

CROSS-REFERENCE TO RELATED APPLICATIONS

This application is a continuation of U.S. patent application Ser. No. 11/225,659, filed on Sep. 12, 2005, now U.S. Pat. No. 8,298,389, which is incorporated herein by reference.

FIELD OF THE INVENTION

This invention relates to electrochemical sensors for the detection of analyte

BACKGROUND OF THE INVENTION

Electrochemical analytical sensors are commonly used to determine the presence and concentration of a biological analyte. Such sensors are used, for example, to monitor blood glucose levels in diabetic patients.

Although many currently available sensor strip products require relatively large sample volumes, e.g., generally requiring 3 µL or more of blood or other biological fluid, there has been a trend for small volume sizes, such as 1 µL and less. For example, U.S. Pat. Nos. 6,143,164, 6,338,790 and 6,616,819 provide various configurations of small volume (i.e., less than 1 µL), disposable sensors. These patents suggest that sensors with sample chamber volumes of 0.5 µL, 0.25 µL, and even 0.1 µL can be made.

However, as the volume of sample chambers in the sensors decreases, it becomes increasingly more difficult to fill the sample chamber with an accurate amount of the sample to be analyzed, in part due to the small area available through which the sample enters. Additionally, as the sample chamber volume decreases, there is increased difficulty in repeatedly manufacturing the small volume sample chamber.

As electrochemical sensors continue to be used, there continues to be an interest in electrochemical sensors that utilize a small sample volume of biological fluid for analysis.

SUMMARY OF THE INVENTION

The electrochemical sensor strips of the present invention have a configuration that allows accurate and repeatable analysis of a sample of biological fluid having a small volume, e.g., a volume of about 0.2 µL or less. Indeed, in accordance with the subject invention sample volumes of as little as 0.15 µL, and even 0.1 µL, 0.05 µL and 0.03 µL, can be accurately and reproducibly tested for the level of analyte.

Embodiments of the sensors strips of the present invention include two substrates forming the overall sensor construction, a spacer between the substrates, a working electrode, a counter electrode, and an indicator electrode positioned downstream of the working electrode. Together, the two substrates and spacer define a sample chamber between the substrates, the sample chamber having a sample inlet. The working electrode, counter electrode, and indictor electrode are present in the sample chamber, the working and counter electrodes being facing electrodes, with the working electrode present between the inlet to the sample chamber and the indictor electrode. A measurement zone is present within the sample chamber. Embodiments include measurement zones configured so that a small volume of sample, such as no more than about 0.2 µL, of sample, e.g., no more than about 0.15 µL, e.g., no more than about 0.1 µL, and e.g., no more than about 0.05 µL of sample, is needed to obtain an accurate analyte level reading. Embodiments also include samples of no more than about 0.3 µL.

The distance between the working and counter electrodes is less than the axial length of the measurement zone, e.g., this distance may be less than about 10%, e.g., less than about 5%, e.g., about 1-10% or about 1-5%, of the axial length of the measurement zone.

The sensors of the present invention are used for the detection and quantification of an analyte, typically glucose, in very small volume, submicroliter samples. In general, the invention is a sensor for analysis of an analyte in a small volume of sample by, for example, coulometry, amperometry, potentiometry or any combination thereof. A sensor strip of the invention may utilize a non-leachable or non-diffusible or leachable or diffusible mediator. In many instances, the sensor strip may additionally or alternately utilize a non-leachable or non-diffusible or leachable or diffusible electron transfer agent, such as an enzyme.

In one particular aspect, the invention is directed to a sensor for determining the concentration of an analyte in a sample, with the sensor having a sample chamber having a volume, and a measurement zone within the sample chamber, the measurement zone having a volume less than the volume of the sample chamber. A working electrode and a counter electrode are opposed to one another in the measurement zone. The distance between the working electrode and the counter electrode is less than the axial length of the measurement zone. This distance may be less than about 10% of the axial length of the measurement zone, or less than about 5%. The sensor may include a spacer, which has a thickness that is less than the overlap of the electrodes along their axial length, which may be less than about 10% of the axial length, such as about 1-10%, or less than 5% of the axial length, such as about 1-5%.

In another particular aspect, the invention is directed to a sensor strip that has a first substrate and a second substrate, and a sample chamber present between the first substrate and the second substrate. The sample chamber has a volume of no more than 1 µL, and has present therein a working electrode on the first substrate and a counter electrode on the second substrate opposed to the working electrode. Together, the working electrode and the counter electrode form an electrode overlap, with the distance between the electrodes being no more than the axial length of the overlap. An indicator electrode is present on one of the substrates, and is positioned so that the working electrode is between the indicator electrode and the inlet to the sample chamber. The sensor includes a measurement zone having a volume less than the volume of the sample chamber, with the measurement zone defined by the electrode overlap.

In yet another particular aspect, the invention is directed to a sensor having a first substrate and a second substrate and a spacer between the substrates. The spacer has a thickness of no greater than 0.5 mm. Together, the spacer and first and second substrates define a sample chamber having a volume of no more than 1 microliter. Located within the sample chamber are a working electrode on the first substrate, and a counter electrode on the second substrate and opposed to or in opposite relation to the working electrode, together the working electrode and the counter electrode forming an electrode overlap. The spacer thickness is no more than 10% of the electrode overlap length. There is also a measurement zone within the sample chamber, the measurement zone positioned between the working electrode and the counter electrode and extending along the electrode overlap, the measurement zone having a volume of no more than 0.2 microliter. An indicator electrode is present within the sample chamber and not within the measurement zone.

The volume of the measurement zone, for each or any of the aspects of this invention, could be no more than 0.2 μL, no more than 0.15 μL, no more than 0.1 μL, and no more than 0.05 μL.

This invention is also directed to device kits, which include at least one sensor according to the invention, and a meter (configured for operably receiving the sensor) and/or a lancing device.

Systems for determining analyte concentration in a sample are also an aspect of the invention. In one embodiment, a system includes an analyte sensor for receiving the sample to be tested, and a meter, with the sensor operably connected to the meter.

This invention is also directed to methods of determining the concentration of an analyte in a sample. The methods include providing a sensor, such as any of those described above, drawing the sample into the measurement zone, and analyzing the analyte concentration in the sample. The analysis may be done by coulometry or amperometry.

Alternate methods include drawing the sample into the measurement zone so that the sample contacts the working electrode and the counter electrode and determining analyte concentration in the sample in the measurement zone.

These and various other features which characterize the invention are pointed out with particularity in the attached claims. For a better understanding of the sensor strips of the invention, their advantages, their use and objectives obtained by their use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views:

FIG. 1 is a schematic, perspective view of an exemplary embodiment of an electrochemical sensor strip in accordance with the principles of the present invention;

FIG. 2 is a top view of an embodiment of the sensor strip of FIG. 1;

FIG. 3 is a top view of an alternate embodiment of the sensor strip of FIG. 1;

DETAILED DESCRIPTION

Figure 4:
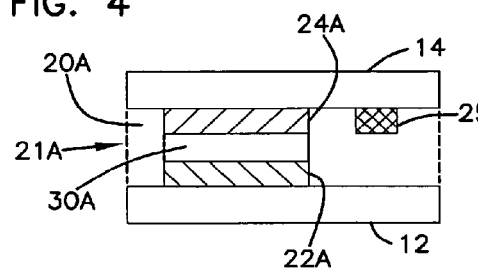
FIG. 4 is an enlarged side view of a first embodiment of a sample chamber configuration suitable for the sensor strips of FIGS. 1, 2 and 3.

The present invention is directed to small volume, in vitro analyte electrochemical sensors in which the measurement zone only partially fills the sample chamber volume. The sensors use a smaller biological fluid sample volume to obtain an accurate analyte reading than do previous sensor strips in which the entire sample chamber needs to be filled. The sensor strips of the present invention include a facing two-electrode system with an additional indicator electrode positioned downstream of the facing electrodes. With such a configuration, and when used with, e.g., coulometric techniques, the volume of the sample analyzed is the sample present between the two facing electrodes. This volume between the two facing electrodes is the measurement zone.

Embodiments of the subject invention include sensors having a measurement zone that has a submicroliter volume, e.g., a volume of no more than about 0.2 μL, e.g., no more than about 0.15 μL, e.g., no more than about 0.1 μL. In some embodiments, the volume of the measurement zone may be as low as about 0.05 μL or as low as about 0.03 μL or less. The subject devices may be adapted for use with any biological fluid. For example, the biological fluid may be, but is not limited to, blood, serum, interstitial fluid, urine, tears, sweat, and the like. Likewise, the subject devices may be used to determine the concentration of a variety of analytes including but not limited to, glucose, lactate, and the like.

Because only a portion of the sample volume present in the sample chamber is analyzed and the additional sample present within the sample chamber is not analyzed, the measurement accuracy is not dependent on the total amount of sample present in the sample chamber. The sensors of the present invention can determine the analyte concentration of a sample that does not fill the entire sample chamber; that is, it is not necessary that the sample chamber be completely filled with sample in order to obtain an accurate analyte concentration.

As stated, an indicator electrode can be positioned downstream of the facing two-electrode system, which includes at least one working electrode and one counter electrode. The analyte assay will not initiate until the indicator electrode has been triggered, thus ensuring the presence of the desired volume between the facing electrodes.

To obtain accurate analyte measurement, particularly when using coulometry for the assay, the sample in the measurement zone may be non-flowing, i.e., the flow through the measurement zone and sample chamber has been stopped, to ensure a fixed sample volume. In some embodiments, an indicator electrode can be configured to determine whether or not sample flow has stopped.

When used herein, the following definitions define the stated term:

A "biological fluid" is any body fluid in which the analyte can be measured, for example, blood, interstitial fluid, dermal fluid, sweat, and tears. "Blood" includes whole blood and its cell-free components, such as, plasma and serum.

A "counter electrode" refers to an electrode, used in conjunction with a working electrode, through which passes an electrochemical current equal in magnitude and opposite in sign to the current passed through the working electrode. The term "counter electrode" is meant to include counter electrodes which also function as reference electrodes (i.e. a counter/reference electrode) unless the description provides that a "counter electrode" excludes a reference or counter/reference electrode.

"Downstream" refers to a relative position that this later in the path, or that is contacted later; e.g., a downstream electrode is contacted by biological fluid sample after an upstream electrode has been contacted by that same sample.

An "electrochemical sensor" or "electrochemical sensor strip", and variations thereof, is a device configured to detect the presence of and/or measure the concentration of an analyte via electrochemical oxidation and reduction reactions. These reactions are transduced to an electrical signal that can be correlated to an amount or concentration of analyte. An electrochemical sensor may be configured as an elongated strip or otherwise.

"Electrolysis" is the electrooxidation or electroreduction of a compound either directly at an electrode or via one or more electron transfer agents (e.g., redox mediators and/or enzymes).

An "electron transfer agent" is a molecule that carries electrons between either a redox mediator and the analyte or the working electrode and the analyte. An electron transfer agent may be used in combination with a redox mediator.

The term "facing electrodes" refers to a configuration of the working and counter electrodes in which the working surface of the working electrode is disposed in approximate opposition to a surface of the counter electrode.

An "indicator electrode" includes one or more electrodes that detect partial or complete filling of a sample chamber and/or measurement zone with biological fluid sample.

A "layer" includes one or more layers.

The "measurement zone" is defined herein as a region of the sample chamber sized to contain only that portion of the sample present between the working and counter electrodes that is to be interrogated during an analyte assay.

A "non-diffusible," "non-leachable," or "non-releasable" compound is a compound which does not substantially diffuse away from the working surface of the working electrode for the duration of the analyte assay.

A "redox mediator" is an agent for carrying electrons between the analyte and the working electrode, either directly, or via an electron transfer agent.

A "reference electrode" includes a reference electrode that also functions as a counter electrode (i.e., a counter/reference electrode) unless the description provides that a "reference electrode" excludes a counter/reference electrode.

A "working electrode" is an electrode at which analyte is electrooxidized or electroreduced with or without the agency of a redox mediator.

Referring to the Drawings in general and FIG. 1 in particular, a small volume, in vitro electrochemical sensor strip 10 of the invention is schematically illustrated. Sensor strip 10 has a first substrate 12, a second substrate 14, and a spacer 15 positioned therebetween. As will be described below, sensor strip 10 includes at least one working electrode, at least one counter electrode, and at least one indicator electrode. Sensor strip 10 is a layered construction, in certain embodiments having a generally rectangular shape, i.e., its length is longer than its width, although other shapes are possible as well.

The basics of sensor strips such as strip 10 are generally known. The strip has a distal end and an opposite proximal end, which is generally configured and arranged for insertion into a sensor reader. Various specific constructions of sensor strips can be found, for example, in U.S. Pat. Nos. 6,143,164, 6,338,790 and 6,616,819.

The dimensions of a sensor may vary. In certain embodiments, the overall length of sensor strip 10 may be no less than about 20 mm and no greater than about 50 mm. For example, the length may be between about 30 and 45 mm; e.g., about 30 to 40 mm. It is understood, however that shorter and longer sensor strips 10 could be made. In certain embodiments, the overall width of sensor strip 10 may be no less than about 3 mm and no greater than about 10 mm. For example, the width may be between about 4 and 8 mm; about 5 to 6 mm. In one particular example, sensor strip 10 has a length of about 32 mm and a width of about 6 mm. In another particular example, sensor strip 10 has a length of about 40 mm and a width of about 5 mm. In yet another particular example, sensor strip 10 has a length of about 34 mm and a width of about 5 mm.

Substrates

As provided above, sensor strip 10 has first and second substrates 12, 14, non-conducting, inert substrates which form the overall shape and size of sensor strip 10. Substrates 12, 14 may be substantially rigid or substantially flexible. In certain embodiments, substrates 12, 14 are flexible or deformable. Examples of suitable materials for substrates 12, 14 include but are not limited to polyester, polyethylene, polycarbonate, polypropylene, nylon, and other "plastics" or polymers. In certain embodiments the substrate material is "Melinex" polyester. Other non-conducting materials may also be used.

Spacer Layer

As indicated above, positioned between substrate 12 and substrate 14 is spacer 15. Spacer 15 separates first substrate 12 from second substrate 14. Spacer 15 is an inert non-conducting substrate, typically at least as flexible and deformable (or as rigid) as substrates 12, 14. In certain embodiments, spacer 15 is an adhesive layer or double-sided adhesive tape or film. Any adhesive selected for spacer 15 should be selected to not diffuse or release material which may interfere with accurate analyte measurement.

In certain embodiments, the thickness of spacer 15 may be at about least 0.01 mm (10 µm) and no greater than about 1 mm or 0.5 mm. For example, the thickness may be between about 0.02 mm (20 µm) and 0.2 mm (200 µm). In one certain embodiment, the thickness is about 0.05 mm (50 µm), and about 0.1 mm (100 µm) in another embodiment.

Sample Chamber

Still referring to FIG. 1 and also to FIG. 2, sensor strip 10 includes a sample chamber 20 for receiving a volume of sample to be analyzed. Sample chamber 20 is configured so that when a sample is provided in chamber 20, the sample is in electrolytic contact with both the working electrode and the counter electrode, which allows electrical current to flow between the electrodes to effect the electrolysis (electrooxidation or electroreduction) of the analyte. Sample chamber 20 has an inlet 21 for receiving the sample.

Sample chamber 20 is defined by substrate 12, substrate 14 and spacer 15; specifically sample chamber 20 exists between substrate 12 and substrate 14 where spacer 15 is not present. Typically, a portion of spacer 15 is removed to provide an area between substrates 12, 14 without spacer 15; this volume of removed spacer is sample chamber 20.

Referring to FIG. 2, a top view of sensor strip 10 is illustrated. From this view, sample chamber 20 extends from a first side edge of sensor strip 10 to the opposite second side edge. One of the ends of sample chamber 20 includes inlet 21; thus, sensor strip 10 is a "side fill" sensor. Sensor strip 10 may include printing or other indicia to indicate which side is inlet 21. It will be understood that the sensor could alternatively or additionally be configured as an "end fill" sensor (see for example FIG. 3) and/or a "top fill" sensor. Also indicated in FIG. 2 is a measurement zone 30, which will be discussed in detail below.

Referring to FIG. 3, a top view of an alternate sensor strip 10' is illustrated. For this example from this view, sample chamber 20' extends from the distal end of the sensor to both side edges for venting. Sample chamber 20' includes inlet 21' at the distal end; thus, sensor strip 10' is an "end fill" sensor. Also indicated in FIG. 3 is a measurement zone 30'. For the following discussion, although the term "sample chamber 20" is used, both sample chambers 20, 20' are included in the discussion.

The volume of sample chamber 20 is generally the thickness of spacer 15 times the area of spacer 15 removed. This thickness is small to promote rapid electrolysis of the analyte, as more of the sample will be in contact with the electrode surface for a given sample volume. In addition, a thin sample chamber 20 helps to reduce errors from diffusion of analyte into the measurement zone from other portions of the sample chamber during the analyte assay, because diffusion time is long relative to the measurement time, which may be about 5 seconds or less.

Sample chamber 20 has a small volume, e.g., volumes may range from about a few microliters to about 2 µL or 1 µL or less, such as submicroliter volumes. For example, sample chamber 20 may have a volume that is no more than about 5 µL, e.g., no more than about 1 µL, e.g., no more than about 0.5 µL.

Electrodes

As provided above, sensor strip 10 includes a working electrode, a counter electrode, and an indicator electrode. The counter electrode may be a counter/reference electrode or a reference electrode. If multiple counter electrodes are present, one of the counter electrodes will be a counter electrode and one or more may be reference electrodes. Referring to FIGS. 4 through 8, four examples of suitable electrode configurations are illustrated. In each of the configurations, the working electrode is designated with reference numeral 22, the counter electrode is designated with reference numeral 24, and the indicator electrode is designated with reference numeral 25. These reference numerals include an alphabetic suffix to indicate the configuration embodiment. For general discussions, working electrodes will be referred to collectively as working electrode 22, counter electrodes will be referred to collectively as counter electrode 24, and indicator electrodes will be referred to collectively as indicator electrode 25.

To facilitate understanding of the construction of sensor strip 10 and electrodes 22, 24, 25, the following nomenclature will be used. The length of any electrode 22, 24, is the axial dimension along the sample movement direction. The width of any electrode 22, 24, 25 is the dimension in the transverse direction. It should be understood that in FIGS. 4, 6 and 7, the electrodes have been illustrated as having a substantial thickness; this has been done to facilitate understanding of their placement and the overall structure. Typically the electrodes will be very thin, depending on the method by which the electrodes are formed; for example, a screen-printed electrode is usually at least a few micrometers thick, whereas sputtered or electrodeposited electrodes are usually submicron in thickness.

Working Electrode

Figure 5:
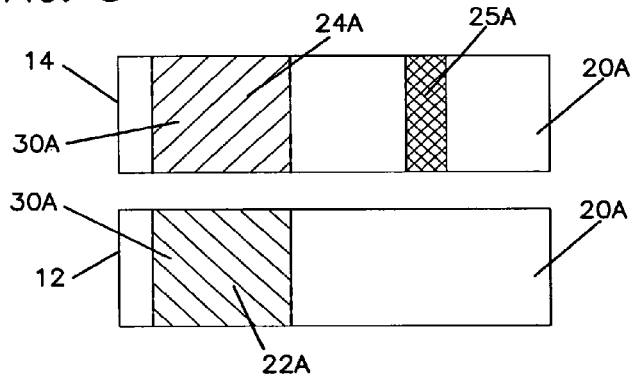
FIG. 5 is a top plan view of the sample chamber configuration of FIG. 4, illustrated with the substrates in an exploded configuration.

A working electrode is positioned on first substrate 12. Referring to FIGS. 4 and 5, working electrode 22A is illustrated on substrate 12; in FIG. 6, working electrode 22B is on substrate 12; in FIG. 7, working electrode 22C is on substrate 12; and in FIG. 8, working electrode 22D is on substrate 12. For general discussions, all working electrodes 22A, 22B, 22C, 22D will be referred to collectively as working electrode 22.

Working electrode 22 is a layer of conductive material such as gold, carbon, platinum, ruthenium dioxide, palladium, or other non-corroding, conducting material. An example of a suitable conductive epoxy is ECCOCOAT CT5079-3 Carbon-Filled Conductive Epoxy Coating (available from W.R. Grace Company, Woburn, Mass.).

Working electrode 22 may be applied on substrate 12 by any of various methods. Electrode 22 may be deposited, such as by vapor deposition or vacuum deposition, sputtered, printed on a flat surface or in an embossed or otherwise recessed surface, transferred from a separate carrier or liner, etched, or molded. Screen-printing is a preferred method for applying working electrode 22, although other methods such as piezoelectric printing, ink jet printing, laser printing, photolithography, and painting can be used.

The material of working electrode 22 typically has relatively low electrical resistance and is typically electrochemically inert over the potential range of the sensor during operation.

Working electrode 22 is provided in measurement zone 30 for the analysis of analyte, in conjunction with the counter electrode, as will be described below. Specifically, working electrode 22A is within measurement zone 30A, working electrode 22B is within measurement zone 30B working electrode 22C is within measurement zone 30C, and working electrode 22D is within measurement zone 30D.

Sensing Chemistry

In addition to working electrode 22, sensing chemistry material(s) are preferably provided in measurement zone 30 for the analysis of the analyte. Sensing chemistry material facilitates the transfer of electrons between working electrode 22 and the analyte in the sample. Any sensing chemistry may be used in sensor strip 10; the sensing chemistry may include one or more materials.

The sensing chemistry can be diffusible or leachable, or non-diffusible or non-leachable. For purposes of discussion herein, the term "diffusible" will be used to represent "diffusible or leachable" and the term "non-diffusible" will be used to represent "non-diffusible or non-leachable" and variations thereof. Placement of sensing chemistry components may depend on whether they are diffusible or not. For example, both non-diffusible and/or diffusible component(s) may form a sensing layer on working electrode 22. Alternatively, one or more diffusible components may be present on any surface in sample chamber 20 or measurement zone 30 prior to the introduction of the sample to be analyzed. As another example, one or more diffusible component(s) may be placed in the sample prior to introduction of the sample into sample chamber 20 and measurement zone 30.

Electron Transfer Agent

The sensing chemistry generally includes an electron transfer agent that facilitates the transfer of electrons to or from the analyte. The electron transfer agent may be diffusible or non-diffusible, and may be present on working electrode 22 as a layer. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes can be used for other analytes.

The electron transfer agent, whether it is diffusible or not, facilitates a current between working electrode 22 and the analyte and enables the electrochemical analysis of molecules. The agent facilitates the transfer electrons between the electrode and the analyte.

Redox Mediator

This sensing chemistry may, additionally to or alternatively to the electron transfer agent, include a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator can be a polymeric redox mediator, or, a redox polymer (i.e., a polymer having one or more redox species). Examples of suitable redox mediators and redox polymer are disclosed in U.S. Pat. No. 6,338,790, for example, and in U.S. Pat. Nos. 6,605,200 and 6,605,201.

If the redox mediator is non-diffusible, then the redox mediator may be disposed on working electrode 22 as a layer. In an embodiment having a redox mediator and an electron transfer agent, if the redox mediator and electron transfer agent are both non-leachable, then both components are disposed on working electrode 22 as individual layers, or combined and applied as a single layer.

The redox mediator, whether it is diffusible or not, mediates a current between working electrode 22 and the analyte and enables the electrochemical analysis of molecules which may not be suited for direct electrochemical reaction on an electrode. The mediator functions as an agent to transfer electrons between the electrode and the analyte.

Counter Electrode

Sensor strip 10 includes at least one counter electrode positioned on second substrate 14. Referring to FIGS. 4 and 5, counter electrode 24A is illustrated on substrate 14; in FIG. 6, counter electrode 24B is on substrate 14; in FIG. 7, counter electrode 24C is on substrate 14; and in FIG. 8, counter electrode 24D is on substrate 14. For general discussions, all counter electrodes 24A, 24B, 24C, 24D will be referred to collectively as counter electrode 24. Working electrode 22 and counter electrode 24 form a facing electrode pair.

Counter electrode 24 may be constructed in a manner similar to working electrode 22. Counter electrode 24 may also be a counter/reference electrode. Alternatively, a separate reference electrode may be provided in contact with the sample chamber. Suitable materials for counter electrode 24 include carbon, Ag/AgCl or Ag/AgBr applied over a non-conducting base material or silver chloride on a silver metal base. The same materials and methods may be used to make counter electrode 24 as are available for working electrode 22, although different materials and methods may also be used. Counter electrode 24 can include a mix of multiple conducting materials, such as Ag/AgCl and carbon.

Indicator Electrode

Sensor strip 10 includes at least one indicator electrode positioned on one of first substrate 12 and second substrate 14. Referring to FIGS. 4 and 5, indicator electrode 25A is illustrated on substrate 14; in FIG. 6, indicator electrode 25B is on substrate 14 and indicator electrode 25B is on substrate 12; in FIG. 7, indicator electrode 25C is on substrate 12; and in FIG. 8, indicator electrode 25D is on substrate 14 and indicator electrode 25D' is on substrate 12. For general discussions, all indicator electrodes 25A, 25B, 25B', 25C, 25D, 25D' will be referred to collectively as indicator electrode 25. Indicator electrode 25 may be constructed in a manner similar to working electrode 22 and/or counter electrode 24. Suitable materials and methods for indicator electrode 25 include the same materials and methods as used for working electrode 22 and/or counter electrode 24, although different materials and methods may also be used. Carbon is a material that may be used for indicator electrode 25.

Indicator electrode 25 is used to detect when sample chamber 20 has been sufficiently filled, to prevent partial filling of measurement zone 30.

Indicator electrode 25 is positioned in sample chamber 20 with at least working electrode 22 positioned between it and inlet 21. In many embodiments, counter electrode 24 will also be positioned between indicator electrode 25 and inlet 21. Indicator electrode 25 is so positioned so that that biological fluid sample, upon entering sample chamber 20 via inlet 21, flows axially past working electrode 22 prior to contacting indicator electrode 25.

Upon the sample contacting indicator electrode 25, electrode 25 is the source of a signal to the attached meter. Suitable signals include, for example, voltage, current, resistance, impedance, or capacitance. The signal indicates to the meter, and/or the user, that there is sufficient sample in measurement zone 30 to begin the assay. This indication may be a visual sign and/or auditory and/or vibratory signal, or the meter may be configured to automatically initiate the assay.

Electrode Configurations

Working electrode 22 and counter electrode 24 are positioned on opposite substrates in a facing configuration to each other to form a facing electrode pair. Indicator electrode 25 is positioned on either substrate 12, 14, downstream of at least working electrode 22.

Referring to FIGS. 4 and 5, working electrode 22A occupies an inner surface of substrate 12 within sample chamber 20A, and counter electrode 24A occupies an equal area of an inner surface of substrate 14 directly opposite working electrode 22A within sample chamber 20A. That is, working electrode 22A overlaps counter electrode 24A in opposed or opposite relation, forming an electrode overlap that is the same area as each of electrodes 22A, 24A. Indicator electrode 25A occupies a surface of substrate 14 downstream of both working electrode 22A and counter electrode 24A. As shown in FIG. 5, each of working electrode 22A, counter electrode 24A, and indicator electrode 25A extends the transverse width of sample chamber 20A.

Figure 6:
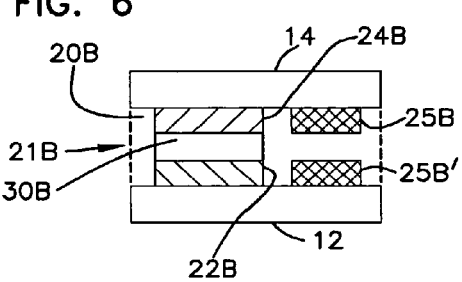
FIG. 6 is an enlarged side view of a second embodiment of a sample chamber configuration suitable for the sensor strips of FIGS. 1, 2 and 3.

Referring to FIG. 6, a second facing electrode configuration is illustrated. Similar to the first configuration, working electrode 22B occupies a surface area of substrate 12 within sample chamber 20B, and counter electrode 24B occupies an equal surface area of substrate 14 directly opposite working electrode 22B within sample chamber 20B. That is, working electrode 22B overlaps counter electrode 24B in opposed or opposite relation, forming an electrode overlap that is the same area as each of electrodes 22B, 24B. In this embodiment, two indicator electrodes 25B, 25B' are present. Indicator electrode 25B occupies a surface of substrate 14 downstream of counter electrode 24B and indicator electrode 25B' occupies a surface of substrate 12 downstream of working electrode 22B. Indicator electrodes 25B, 25B' themselves are facing electrodes. Two indicator electrodes 25B, 25B' may be used to separate the fill detection zone at the indicator electrodes from the real measurement without disturbing the sample present in measurement zone 30B.

Figure 7:
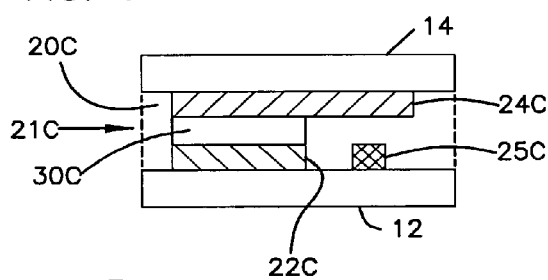
FIG. 7 is an enlarged side view of a third embodiment of a sample chamber configuration suitable for the sensor strips of FIGS. 1, 2 and 3.

Referring to FIG. 7, a third facing electrode configuration is illustrated. Working electrode 22C occupies a surface of substrate 12 within sample chamber 20C, and counter electrode 24C occupies a surface of substrate 14 directly opposite, yet larger in area than, working electrode 22C within sample chamber 20C. The axial length of counter electrode 24C is greater than the axial length of working electrode 22C. This configuration may provide a number of advantages, e.g., manufacturability of the sensor, due to the larger length, and thus ease of manufacture, of counter electrode 24C. Working electrode 22C overlaps only a portion of counter electrode 24C in opposed or opposite relation, forming an electrode overlap that is the length of working electrode 22C. Indicator electrode 25C occupies a surface of substrate 12 downstream of working electrode 22C.

Figure 8:
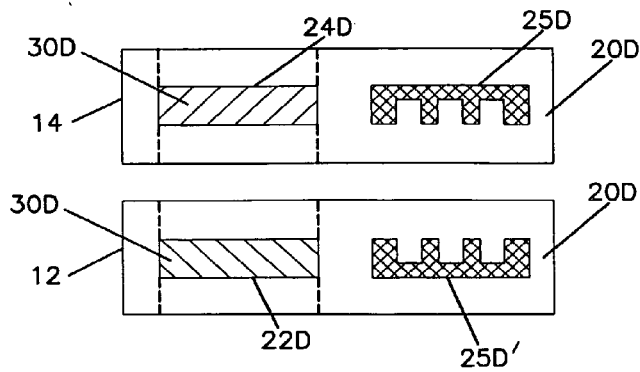
FIG. 8 is a top plan view of a fourth embodiment of a sample chamber configuration, illustrated with the substrates in an exploded configuration.

Referring to FIG. 8, a fourth facing electrode configuration is illustrated. Similar to the second configurations, working electrode 22D occupies a surface area of substrate 12 within sample chamber 20D, and counter electrode 24D occupies an equal surface area of substrate 14 directly opposite working electrode 22D within sample chamber 20D. Working electrode 22D overlaps counter electrode 24D in opposed or opposite relation, forming an electrode overlap that is the same area as each of electrodes 22D, 24D. In this embodiment, two indicator electrodes 25D, 25D' are present. Indicator electrode 25D occupies a surface of substrate 14 downstream of counter electrode 24D and indicator electrode 25D' occupies a surface of substrate 12 downstream of working electrode 22D. Indicator electrodes 25D, 25D' have a plurality of arms or branches that are spaced axially along the length of electrodes 25D, 25D'. Such arms or branches may be used to monitor the flow of sample across indicator electrodes 25D, 25D'. In this embodiment, none of working electrode 22D, counter electrode 24D, nor indicator electrodes 25D, 25' extends the transverse width of sample chamber 20D.

It is noted that the electrodes are typically connected to a conductive trace, not shown in the figures, that extends from the electrode to the proximal end of the sensor. Such traces are used for operatively connecting the electrodes to a meter.

Measurement Zone

Measurement zone 30 is present within sample chamber 20 and is the region of sample chamber 20 that contains that portion of the sample that is interrogated during the analyte assay. Measurement zone 30, in most embodiment, has a volume less than the volume of sample chamber 20; measurement zone 30 thus has a small volume, e.g., about a few microliters to about 1 µL or less, e.g., may have a submicroliter volume. For example, measurement zone 30 may have a volume of no more than about 0.2 µL, e.g., no more than about 0.15 µL, e.g., no more than about 0.1 µL. In some embodiments, the volume of measurement zone 30 is no more than about 0.05 µL or no more than about 0.03 µL. Measurement zone 30 is that volume between working electrode 22 and counter electrode 24.

Measurement zone 30 can have a volume that is equal to the volume of sample chamber 20, although in most embodiments the volume of measurement zone 30 is no more than about 75% of the volume of sample chamber 20, e.g., no more than about 50%, e.g., no more than about 25%. Specific suitable examples of volumes for measurement zone 30 include about 17% and less, about 33% and less, about 50% and less, and about 67% and less of the volume of sample chamber 20.

FIGS. 2 and 3 illustrate, in dashed lines, the position of measurement zone 30, 30' in sample chamber 20, 20'. In these illustrated embodiments, measurement zone 30, 30' is in close proximity to inlet 21, 21'. Additionally, it is readily seen that measurement zone 30, 30' is smaller than sample chamber 20, 20'.

The electrode configurations shown in FIGS. 4 through 8 have been described above. Referring again to FIGS. 4 through 8, the relationship of the measurement zone to the sample chamber, for each of these configurations, will be discussed. In FIGS. 4 and 5, sample chamber 20A and measurement zone 30A are shown; in FIG. 6, sample chamber 20B and measurement zone 30B are shown; in FIG. 7, sample chamber 20C and measurement zone 30C are shown; and in FIG. 8, sample chamber 20D and measurement zone 30D are shown. For general discussions, all sample chambers 20A, 20B, 20C, 20D will be referred to collectively as sample chamber 20 and all measurement zones 30A, 30B, 30C, 30D will be referred to collectively as measurement zone 30.

The measurement zones illustrated in FIGS. 4 through 8 could be measurement zone 30 of FIG. 2, measurement zone 30' of FIG. 3, or be present in yet a different sensor strip with sample chamber configuration. In each of FIGS. 4 through 8, the depiction illustrated is representative of the entire volume of the sample chamber. For example, sample chamber 20A shown in FIGS. 4 and 5 may be sample chamber 20 of FIG. 2, oriented in the same position. That is, referring to FIGS. 2 and 4, a biological fluid sample would enter strip 10 on the left side at inlet 21, 21A and flow in an axial direction to the right into sample chamber 20, 20A and to measurement zone 30, 30A. Within measurement zone 30, 30A, the sample would contact working electrode 22A and counter electrode 24A, contacting the left end edge of electrodes 22A, 24A and then the right end edge. Upon covering electrodes 22A, 24A and filling of measurement zone 30, 30A, the sample would progress further axially to the right to indicator electrode 25A. This axial, left-to-right flow is the direction of flow for all of the electrode configurations in FIGS. 4 through 8.

Referring to FIGS. 4 and 5, measurement zone 30A exists at the electrode overlap, which extends between the axial end edges and the transverse edges of working electrode 22A and counter electrode 24A, which are aligned. That is, the ends of electrodes 22A, 24A do not extend axially or transversely past the other, thus the electrode overlap is the area of both electrodes 22A, 24A. The thickness of measurement zone 30A is the distance between electrodes 22A, 24A. In this embodiment, working electrode 22A and counter electrode 24A, and thus measurement zone 30A, extend transversely to the edges of sample chamber 20A.

Measurement zone 30B of FIG. 6 is similar to measurement zone 30A of FIGS. 4 and 5. Measurement zone 30B exists at the electrode overlap, which extends between the axial end edges and the transverse edge of working electrode 22B and counter electrode 24B, which are aligned and do not extend axially or transversely past one other.

Counter electrode 24C of FIG. 7 occupies more axial length and area than working electrode 22C. In this embodiment, measurement zone 30C is that volume defined by the overlap of electrodes 22C, 24C. The electrode overlap extends only as far as working electrode 22C in the axial direction. The electrode overlap and thus measurement zone 30C does not extend the entire length of counter electrode 24C, but is present only in the axial length of where the sample is interrogated during the assay.

Measurement zone 30D of FIG. 8 is similar to measurement zone 30A of FIGS. 4 and 5 and measurement zone 30B of FIG. 6, except that working electrode 22D and counter electrode 24D, and thus measurement zone 30D, does not extend to the transverse edges of sample chamber 30D. Measurement zone 30D does extend between the axial end edges and transverse edges of working electrode 22D and counter electrode 24D, which are aligned and do not extend past the other.

The volume of measurement zone 30 is the distance between working electrode 22 and counter electrode 24, times the measurement zone 30 length (which is the axial length overlap of electrodes 22, 24), times the measurement zone 30 width (which is the transverse width overlap of electrodes 22, 24). In certain embodiments, the volume is submicroliter, e.g., no more than about 0.2 µL, e.g., no more than about 0.15 µL, e.g., no more than about 0.1 µl. In some embodiments, the volume of measurement zone 30 is no more than about 0.05 µL, or no more than about 0.03 µL. The distance between working electrode 22 and counter electrode 24, which is also the thickness or depth of sample chamber 20, is based on the thickness of spacer 15. As provided above, the thickness of spacer 15, and thus the distance between electrodes 22, 24 may be at least about 0.01 mm (10 µm) and in many embodiments no greater than about 1 mm. Usually this distance is between about 0.02 mm (20 µm) and 0.2 mm (200

µm), e.g., about 0.05 mm (50 µm) or about 0.1 mm (100 µm). In many embodiments, this distance between electrodes 22, 24 is less than the axial length of the measurement zone, e.g., this distance may be less than about 10%, susch as about 1-10%, e.g., less than about 5%, e.g., about 1-5%, e.g., less than about 3%, of the axial length of measurement zone 30, which is defined by the shorter axial length of electrodes 22, 24. Lower levels are preferred, as this increases the measurement accuracy, based on the decreased planar area available for edge diffusion. For this desired percentage, electrodes 22, 24 may extend the transverse width of sample chamber 20.

Application of the Sensor

A common use for the analyte sensor of the present invention, such as sensor strip 10, 10', is for the determination of analyte concentration, such as glucose concentration, in a patient or other user. In many embodiments, sensor strips 10 are available at pharmacies, hospitals, clinics, from doctors, and other sources of medical devices. Multiple sensor strips 10 can be packaged together and sold as a single unit; e.g., a package of 25, 50, or 100 strips.

Sensor strips 10 are generally configured for use with an electrical meter, which can be connected to a PC or other electronics. The connection may be wired or wireless. This meter is available at generally the same locations as sensor strips 10, and sometimes may be packaged together with sensor strips 10.

A lancing device or other mechanism to obtain a sample of biological fluid, e.g., blood, from the patient or user is also generally available at the same locations as sensor strips 10 and the meter, and sometimes may be packaged together with sensor strips 10 and/or meter.

Operation of the Sensor

In use, a sample of biological fluid is provided into the sample chamber of the electrochemical strip, where the level of analyte is determined. In many embodiments, it is the level of glucose in blood that is determined. Also in many embodiments, the source of the biological is a drop of blood drawn from a patient, e.g., after piercing the patient's skin with a lancing device.

The following discussion is directed to sensor strip 10, however, this discussion also applies to sensor strip 10' and other sensor strip configurations. For sensor strip 10, a side fill sensor, sensor strip 10 is brought into contact with the sample of biological fluid so that inlet 21 contacts the sample. Often, sensor strip 10 is operably connected, (in many embodiments, inserted) at its proximal end into a meter. At least a portion of the sample enters sample chamber 20 via inlet 21 and axially flows to measurement zone 30 and working electrode 22 and counter electrode 24.

The meter to which the sensor strip is attached is typically programmed to monitor for when a signal from indicator electrode 25 is received, thus indicating if and when sample has contacted indicator electrode 25. When the signal is received, a sufficient amount of sample has entered sample chamber 20 to ensure that measurement zone 30 is adequately filled, due to the configuration in which indicator electrode 25 is downstream of working electrode 22 and measurement zone 30. The signal may be an on/off signal, or may be a change (either an increase or decrease) in an existing signal.

In many embodiments, only a portion of the sample, e.g., the drop of blood, enters sensor strip 10. When strip 10, particularly inlet 21 is removed from contact with the droop, the sample within sample chamber 20 stops flowing and remains at least substantially stationary. The dimensions of sample chamber 20 inhibit the sample from moving without the source (e.g., the drop) and the sample remains in a generally non-flowing state. In many but not all embodiments, during the analysis, which may take as little as about 5 seconds or less or as much as about 30 seconds or more, the sample is not flowing.

The electrode configuration illustrated in FIG. 8 includes indicator electrodes 25D, 25D' that can be used to confirm that the sample has stopped flowing. Upon removal of the sample source from inlet 21, the sample, which is in contact with at least the left-end of indicator electrodes 25D, 25D', should stop. The meter to which the sensor strip is attached may be programmed to monitor the change in signal from electrodes 25D, 25D'. As the surface area of indicators electrodes 25D, 25D' covered by sample changes (e.g., increases), the signal from electrodes 25D, 25D' changes, showing that sample is still flowing. As stated above, it may be desired in certain instances that during the analysis the sample is not flowing, so that the volume being analyzed is fixed. Especially when using coulometry to determine the level of analyte, the sample should be fixed.

The analyte assay may be done by coulometry, amperometry, potentiometry, or a combination of methods. The method of calculation will be a function of the meter and other electronics configured for use with sensor strip 10. Details regarding meters, electronics, and calculation methods are discussed, for example, in U.S. Pat. No. 6,338,790.

Sensor strip 10 may be operated with or without applying a potential to electrodes 22, 24. In one embodiment, the electrochemical reaction occurs spontaneously and a potential need not be applied between working electrode 22 and counter electrode 24. In another embodiment, a potential is applied between working electrode 22 and counter electrode 24. The potential may be constant or not, and the magnitude of the potential is dependent on the redox mediator. As above, details regarding potential as related to the sensing chemistry and the electrodes are discussed, for example, in U.S. Pat. No. 6,338,790.

During the analyte analysis, analyte present in the biological fluid sample diffuses, thus contributing to the signal measured. There are generally two competing diffusion processes, one process occurring between electrodes 22, 24 and perpendicular to the surface of electrodes 22, 24, and the second process occurring parallel to the surfaces of electrodes 22,24 from regions outside of measurement zone 30. It is desired to minimize the amount of diffusion by the second process; this is effected by reducing the ratio: [electrode 22, 24 width×distance between electrodes 22, 24] to the [electrode 22, 24 width×measurement zone 30 length]. In other words, this is effected by reducing the distance between electrodes 22, 24 to about 1-10%, e.g., less than about 5%, of the axial length of measurement zone 30, e.g., less than about 3%. For example, a distance of 50 µm and a length of 1000 µm provides a value of 5%; a distance of 38 µm and a length of 1000 µm provides a value of 3.75%.

EXAMPLES

The following examples are provided to show analyte sensors in accordance with the present invention. However, it will be understood that the following examples are exemplary only, and are in nowise comprehensive of the many different types of sensors which may be made in accordance with the present invention.

Examples 1-4

Analyte sensor strips were made with four different electrode axial lengths, similar to the layout illustrated in FIG. 6. For each of the examples, the transverse width and axial length of the sample chamber were 1 mm and 6 mm, respectively; the thickness between facing electrodes (i.e., the sample chamber and measurement zone thickness) was 0.05 mm; and the measurement zone axial length was varied from 1 mm, 2 mm, 3 mm to 4 mm. Thus, the chamber volume was 0.3 µL while the volume of the measurement zone was varied: 0.05 µL, 0.10 µL, 0.15 µL, to 0.20 µL, respectively. The axial width of the measurement zone, along with the total volumes of the measurement zones, are provided below:

As a comparison, a separated sensor strip having both the chamber sample volume and measurement zone volume at 0.3 µL was built by extending the working electrode axial length to extend the entire chamber length.

| Example | Axial Length | Volume |
|---|---|---|
| 1 | 1 mm (0.04 inch) | 0.05 µL |
| 2 | 2 mm (0.08 inch) | 0.1 µL |
| 3 | 3 mm (0.12 inch) | 0.15 µL |
| 4 | 4 mm (0.16 inch) | 0.20 µL |
| Comparison | 6 mm (0.24 inch) | 0.30 µL |

Figure 9:
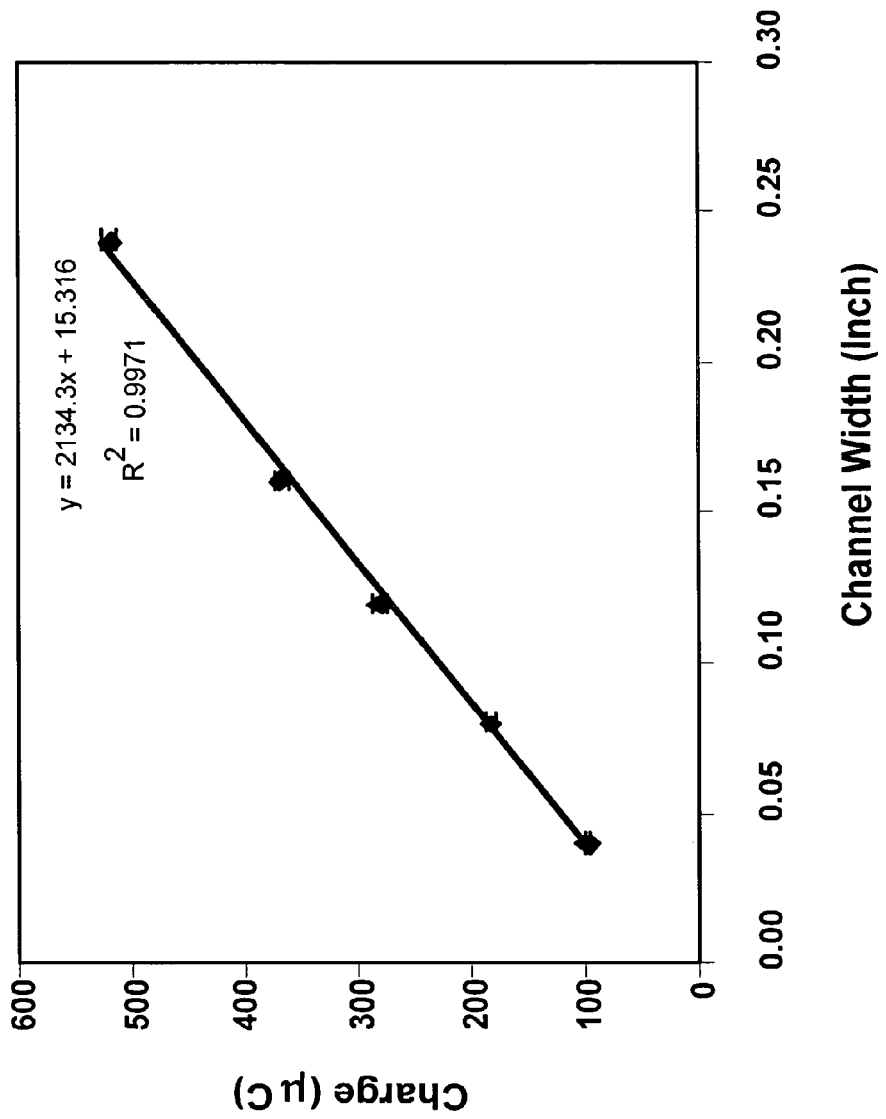
FIG. 9 is a graphical representation of measurement zone length versus charge for a buffered glucose solution.

A glucose in buffer solution was used for to test (n=12/condition) the example sensor. The charges were calculated based on the integration of curves of Current vs. Time measurements. The results were shown in FIG. 9 with standard deviation as the error bars. A linearly relationship can be extended from 6 mm (0.24 inch) to 1 mm (0.04 inch) of electrode axial lengths.

Even though the measurement zones varied from full chamber volume (i.e., comparison example) to only partial chamber volumes (Examples 1-4), the charge was found to be proportional to the volume of the measurement zone. This shows that the edge diffusion of analyte from outside of the measurement zone is insignificant and does not contribute to measurement errors for the electrode configuration tested.

Examples 5-8

Figure 10:
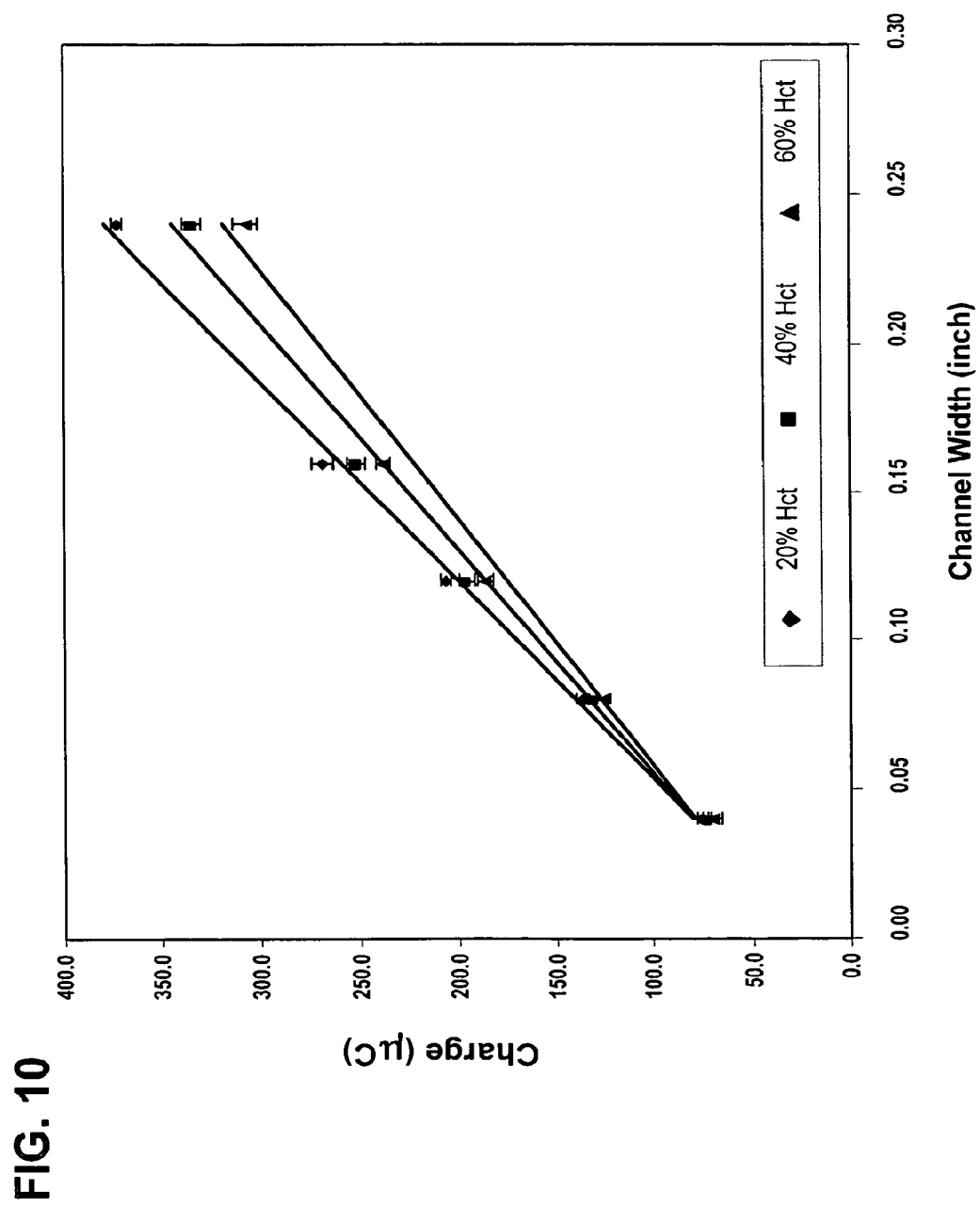
FIG. 10 is a graphical representation of measurement zone length versus charge for blood glucose samples.

Four different analyte sensor strips and the comparison strip were constructed in the same configuration as in Examples 1-4. Blood samples from a single donor adjusted to different hematocrit levels (Hct, 20%, 40% and 60%) were tested. The results are shown in FIG. 10 with the standard deviation as error bars (n=8/condition). The linear relationship was still present for the different blood samples tested. The correlation coefficient $R^2$ of all three linear fittings is higher than 0.98 and the standard deviation of each test is <5%.

The invention has been described with reference to various specific and preferred embodiments and techniques. However, it will be apparent to one of ordinarily skill in the art that many variations and modifications may be made while remaining within the spirit and scope of the invention.

All patents and other references in this specification are indicative of the level of ordinary skill in the art to which this invention pertains. All patents are herein incorporated by reference to the same extent as if each individual patent was specifically and individually incorporated by reference.

What is claimed is:

1. A method of determining the concentration of an analyte in a sample in biological fluid, the method comprising:
   contacting a sample of biological fluid with a sample chamber of an analyte sensor, the sample chamber having a volume;
   filling only a portion of the sample chamber with the sample;
   monitoring a change in an existing signal from an indicator electrode present in the sample chamber;
   determining that the existing signal has not changed during a pre-determined time period; and
   determining the analyte concentration in the sample.

2. The method according to claim 1, wherein determining the analyte concentration in the sample comprises:
   determining the analyte concentration in the sample using only a portion of the sample in the sample chamber.

3. The method according to claim 1, wherein determining the analyte concentration in the sample comprises:
   determining the analyte concentration in the sample using coulometry.

4. The method according to claim 1, wherein determining the analyte concentration in the sample comprises:
   determining the analyte concentration in the sample using amperometry.

5. The method according to claim 1, wherein the sample chamber has a volume of no more than about 1 µL.

6. The method according to claim 1, wherein the sample chamber has a volume of no more than about 0.5 µL.

7. The method according to claim 1, wherein the sample chamber comprises a working electrode, a counter electrode, and another indicator electrode, wherein the working and counter electrodes face each other and wherein the indicator electrodes face each other, wherein the existing signal is from the indicator electrodes.

8. The method according to claim 1, wherein filling only a portion of the sample chamber comprises:
   filling a measurement zone present in the sample chamber, the measurement zone having a volume less than the volume of the sample chamber.

9. The method according to claim 1, further comprising:
   prior to determining the analyte concentration in the sample, determining that a sufficient amount of sample is in the measurement zone.

10. The method according to claim 9, wherein determining that a sufficient amount of sample is in the measurement zone comprises:
    determining that a sufficient amount of sample is in the measurement zone using the indicator electrode.

11. The method according to claim 8, wherein the measurement zone has a volume about 75% or less than the volume of the sample chamber.

12. The method according to claim 8, wherein the measurement zone has an axial length that is less than an axial length of the sample chamber.

13. The method according to claim 8, wherein the measurement zone has a volume no more than about 1 µL.

14. The method according to claim 8, wherein the measurement zone has a volume of no more than about 0.5 µL.

15. The method according to claim 8, wherein the measurement zone has a volume of no more than about 0.2 µL.

16. The method according to claim 8, wherein the measurement zone has a volume of no more than about 0.1 µL.

17. The method according to claim 8, wherein the measurement zone has a volume of no more than about 0.05 µL.

18. The method according to claim 8, wherein the sample chamber has a volume of no more than 1 µL and the measurement zone has a volume of no more than 0.2 µL.

19. The method according to claim 8, wherein the sample chamber comprises a working electrode and a counter electrode, wherein the working and counter electrodes face each other, wherein the distance between the working electrode and the counter electrode is less than about 10% of the axial length of the measurement zone.

20. The method according to claim 8, wherein the measurement zone has a volume that is 17%-67% of the volume of the sample chamber.

* * * * *